United States Patent [19]

Lasker

[11] Patent Number: 5,439,903
[45] Date of Patent: Aug. 8, 1995

[54] ORGANOMETALLIC DIPHENYL HYDRANTOINS AND USES THEREOF

[76] Inventor: Sigmund E. Lasker, Roosevelt Island, N.Y. 10044

[21] Appl. No.: 178,768

[22] Filed: Jan. 7, 1994

Related U.S. Application Data

[63] Continuation of Ser. No. 974,686, Nov. 12, 1992, Pat. No. 5,298,624, which is a continuation of Ser. No. 765,460, Sep. 25, 1991, abandoned, which is a continuation of Ser. No. 363,288, Jun. 2, 1989, abandoned, which is a continuation of Ser. No. 862,160, May 12, 1986, abandoned, which is a continuation of Ser. No. 570,800, Jan. 16, 1984, abandoned.

[51] Int. Cl.$^6$ .................. C07D 233/58; A61K 31/445
[52] U.S. Cl. ..................... 514/184; 548/107; 424/445; 424/447
[58] Field of Search .......................... 548/107; 514/184

[56] References Cited

U.S. PATENT DOCUMENTS

| | | | |
|---|---|---|---|
| 2,118,133 | 5/1938 | Andersen | 548/101 |
| 2,119,701 | 6/1938 | Callsen | 548/101 |
| 2,392,505 | 1/1946 | Rogers | 548/101 |
| 2,955,057 | 10/1960 | Gagliardi et al. | 424/245 X |
| 3,443,013 | 5/1969 | Buc et al. | 424/245 |

OTHER PUBLICATIONS

The Merck Index, 11 ed., published by Merck & Co., Inc. (1989), pp. 1347–1350.
The Merck Index, eighth edition, Stecher, ed., published by Merck & Co., Inc. (1968), pp. 947–949.
Corral, et al., Chemical Abstracts, vol. 51, 2751i (1957).
Hackh's Chemical Dictionary, 3rd ed., McGraw-Hill, N.Y. (1944).
Morrison, et al., Organic Chemistry, 2nd ed., Allyn & Bacon, Inc., Boston, (1966).
Tamayo, et al. (I), Chemical Abstracts, vol. 41, 4056f-g (1947).
Tamayo, et al. (II), Chemical Abstracts, vol. 42, 2893d-f (1948).
Stamm, et al., Chemical Abstracts, vol. 74, 15758e (1971).
Bult, Chemical Abstracts, vol. 85, 25322z (1976).
Malik, et al., Chemical Abstracts, vol. 90, 46,811b (1979), Chemical Subject Index p. 2959c.
Shimazu, et al. (I), Chemical Abstracts, vol. 92, 156241q (1980).
Shimazu, et al. (II), Chemical Abstracts, vol. 93, 85909w (1980).
Sandoval-Rojas, et al., Chemical Abstracts, vol. 100, 109038c (1984).

*Primary Examiner*—John M. Ford

[57] ABSTRACT

Stable, organometallic complexes of 5,5-diphenyl-2,4 imidazolidenedione (diphenyl hydantoin) are versatile biocides, effective when applied topically or parenterally to animal tissue, and when applied topically to plants. The diphenyl Hydantoin complexes are seen to prevent animal and plant tissue infections, and may be combined with other materials to inhibit infection.

4 Claims, No Drawings

ORGANOMETALLIC DIPHENYL HYDRANTOINS AND USES THEREOF

This is a continuation of Ser. No. 07/974,686, filed Nov. 12, 1992, now U.S. Pat. No. 5,298,624, which, in turn, is a continuation of Ser. No. 07/765,460, filed Sep. 25, 1991, (abandoned) which, in turn, is a continuation of Ser. No. 07/363,288, filed Jun. 2, 1989, (abandoned) which, in turn, is a continuation of Ser. No. 06/862,160, filed May 12, 1986, (abandoned) which, in turn, is a continuation of Ser. No. 06/570,800, filed Jan. 16, 1984 (abandoned).

BACKGROUND OF THE INVENTION

The compound 5,5-Diphenyl-2, 4 imidazolidinedione, also known as diphenyl hydantoin, or phenytoin, possesses the structure

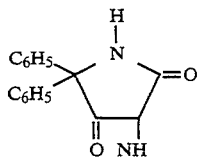

and has been used as an anticonvulsant. It is still used in this way, although it has been supplanted, to some degree, by other drugs, especially the hypnotics. See, e.g., F. Buchtal et al., *Antileptic Drugs,* Raven Press, N.Y., 1972 at page 103. It is more extensively used as a veterinary anticonvulsant, particularly in the treatment of cats.

Diphenyl hydantoin, its derivatives, and compositions containing these are known in the art, as may be seen in, e.g. U.S. Pat. Nos. 2,409,754; 3,932,449; 3,798,233; 4,091,233; and 4,093,809, the disclosures of which are incorporated by reference herein. While many uses for hydantoin and its derivatives are disclosed in these references, it is apparent that hydantoin and its derivatives have never been employed as biocides.

Organometallic compounds have been employed in the past as specific biocides, particularly as antimicrobials. For example, organometallic derivatives of sulfadiazine are among the most prominent of these materials. See, e.g. U.S. Pat. Nos. 3,761,590; 4,020,150; 4,049,802; 3,792,161; and 4,078,058, in which organometallic compounds of sulfadiazine are disclosed, such as silver sulfadizine, zinc sulfadiazine, and cerium sulfadiazine. The efficacy of these compounds as antimicrobials is clear from these disclosures, which are incorporated by reference herein.

While each of these complexes exhibits satisfactory effect in particular applications, no single one of these compounds, or classes of compounds, is effective against a broad range of infections and infective agents such as bacteria, viruses, plasmodia, and the like. Additionally, treatment of target infections with the known metallic complexes of, e.g., sulfadiazne, has resulted in the development of mutant strains against which previously satisfactory anti-infection agents are now less effective, or noneffective.

Hence it is an object of this invention to provide material useful as a versatile biocide for, but not limited to, bacteria, viruses, plasmodia, and the like.

It is a further object of this invention to provide a process for the production of a versatile biocide.

It is a further object of this invention to provide a method of treatment for treating and/or preventing infection in plant and animal tissue by application of a versatile biocide.

How these and other objects of the invention are accomplished will become apparent in the following disclosure.

SUMMARY OF THE INVENTION

The compound 5, 5-Diphenyl-2, 4 imidazolidinedione, i.e., diphenyl hydantoin or phenytoin is reacted with compounds containing metallic ions under conditions favorable to production of complexes of the form Me(Ph), where Me stands for a metal ion, which may be chosen from, e.g., Ag, Zn, Cu, Ce, Fe, and Hg and the like, and Ph stands for diphenyl hydantoin. The resulting organometallic compounds are useful as biocides in the treatment of various plant and animal infections, such as bacterial infections, viral infections, fungal infections, parasite infections, and infection by insects or other pests.

The resulting organometallic complexes are then applied, either topically or parenterally to plant and/or animal tissue so as to prevent or to treat an infection. Additionally, the organometallic complexes may be combined in materials which are designed to prevent infestation or infection, or to relieve infection.

The fact that low toxicity toward host tissue is observed, particularly in the case of the argentometallic complex, renders the complex suitable for use as, e.g., a topical agent in burn therapy or in the treatment of the umbilical stump of newborn infants.

Of particular importance is the argometallic compound referred to herein as silver diphenyl hydantoin. In comparative tests, silver diphenyl hydantoin produced results superior to those obtained using silver sulfadiazine or sodium sulfadiazine, two compounds of choice in surface wound and burn therapy.

DETAILED DESCRIPTION OF THE INVENTION

Diphenyl Hydantoin is first converted to its ammonium salt by reacting it with ammonium hydroxide under conditions favoring formation of the ammonium salt. Following formation of the ammonium salt, a source of the metal ion with which the diphenyl hydantoin is to be complexed is added. This may be, e.g. Silver Nitrate solution, when the desired product is silver diphenyl hydantoin, but may be any appropriate material which contains the metallic ion sought to be complexed. Some of the metallic ions which may be so complexed are the ions of Ag, Zn, Cu, Ce, Fe, and Hg, among others. The source of metallic ions is added under conditions favoring formation of the organmetallic-diphenyl hydantoin complex. The resulting complexes are, in general, poorly soluble, so the formation of a precipitate may be taken as a sign that the complex has formed. Silver diphenyl hydantoin, for example is very insoluble, and precipitates out of the reaction solution almost immediately. Upon precipitation, the metal diphenyl hydantoin is collected, washed free of reactant and ions, and is then dried and readied for use.

The following examples set forth uses of the argentometallic complex silver diphenyl hydantoin in various situations. The fact that silver diphenyl hydantoin alone is used should not be taken to limit the scope of this invention in any way.

The poor solubility of silver diphenyl hydantoin in aqueous media, as well as its poor diffusibility in agar media, required special techniques to achieve usable results. To this end, it was necessary to quantitate action by using a doubling dilution procedure, in Miller-Hinton broth, so as to yield reproducible results.

EXAMPLE I

The effect of silver diphenyl hydantoin at various concentrations upon various microorganisms was tested. For each of the microorganisms listed below, a culture was grown in Miller-Hinton broth (24 hour culture), and then diluted at a 1:100 ratio. This diluted culture was then grown for an additional two hours, after which the silver diphenyl hydantoin was added. Evaluation of the culture took place 18 hours after the addition of the silver phenytoin. The results are summarized in accompanying Table 1, which follows on the next page.

TABLE I

Effect of Silver Phenytoin on Various Microorganisms
Minimal Inhibitory Concentration
Micrograms of Silver Diphenyl Hydantoin per Milliliter

| Organism | 1 | 10 | 20 | 40 |
|---|---|---|---|---|
| Enterococcus (Group D Strep) | − | − | + | ++ |
| Candida Albicans | − | − | + | + |
| Klebsiella | + | + | + | ++ |
| Seratia | − | + | + | + |
| Pseudomonas aeruginosa | − | − | + | + |
| Staphloccoccus aereus | − | − | + | + |

+ = inhibition.
Organisms grown in Miller-Hinton broth.

A 24 hour culture was diluted 1:100 and compound was added to a two hour culture of this dilution and evaluated at 18 hours.

Antibacterial action was also demonstrated in pure cultures of organisms on blood agar plates.

EXAMPLE 2

Experiments designed to compare the effect of Sodium Sulfadiazine, Silver Sulfadiazine, and Silver Diphenyl hydantoin were performed. The parameters of the experiments were identical to those set forth in Example 1, and the results are summarized in Table 2.

TABLE 2

| MINIBAL INHIBITORY CONCENTRATIONS | | | | | | | | | | | | | | | | | | |
|---|---|---|---|---|---|---|---|---|---|---|---|---|---|---|---|---|---|---|
| | Enterococcus | | | Candida A. | | | Klebsiella P. | | | Seratia M. | | | Pseudomonas A. | | | Strep A. | | |
| | S | SS | SP | S | SS | SP | S | SS | SP | S | SS | SP | S | SS | SP | S | SS | SP |
| Microgram of agent | | | | | | | | | | | | | | | | | | |
| 1 | − | − | − | − | − | − | − | − | + | − | − | − | − | − | − | − | − | − |
| 10 | − | − | − | − | − | − | − | − | + | − | + | + | − | + | − | − | − | − |
| 20 | − | − | + | − | − | + | − | + | + | ± | + | + | − | + | + | − | + | + |
| 40 | − | + | ++ | − | − | + | − | + | ++ | ± | + | ++ | − | + | + | + | + | + |

Organisms were grown in Miller-Hinton broth. A twenty-four hour culture was diluted 1:100. Compounds were added to two hour cultures and examined for inhibition at 18 hours. The magnitude of inhibition is estimated and indicated by +.
S: SODIUM SULPHADIMENE
SS: SILVER SULPHADIAZINE
SP: SILVER DIPHENYL HYDANTOIN

EXAMPLE 3

The efficacy of silver diphenyl hydantoin as a plant fungicide was tested. Silver diphenyl hydantoin and commercial fungicide standards were ground and suspended in acetone in an amount equal to 6% of their final volume and then suspended in purified water containing 250 ppm of the surfactant TREM 014 (polyhydric alcohol esters).

In the preventive tests, which are summarized in Tables 3–6, the suspensions were sprayed to the point of run-off on the plants, and were then inoculated 24 hours later with a spore suspension of the fungus as given in Tables 3–6. The thus treated plants were then placed in a saturated humidity chamber at 20° C. for 24 hours, and then in a growth room for an additional 7–12 days. Disease ratings were then made, and recorded as percent disease control.

Curative tests were conducted in a similar matter, except that inoculation with spore fungus took place 24 hours prior to application of the chemical. The results are summarized in Tables 3–6, which follow.

TABLE 3

Evaluation of silver diphenyl hydantoin for the control of grape downy mildew (*Plasmopara viticola*)[1]

| Compound | Concentration[2] | Percent Disease Control | |
|---|---|---|---|
| | | Preventive[3] | Curative[4] |
| Silver diphenyl hydantoin | 100 | 87 | 0 |
| | 20 | 49 | 0 |
| | 5 | 24 | 0 |
| Curzate ® | 100 | 100 | 100 |
| | 20 | 0 | 100 |
| | 5 | 0 | 0 |
| Manzate ® | 100 | 100 | 0 |
| | 20 | 80 | −[5] |
| | 5 | 40 | — |

[1]Test plants incoculated with an aqueous sporangial suspension (1.0 × 10[5] sporangia/ml).
[2]ppm.
[3]Test plants inoculated 24 hours after application of chemical.
[4]Test plants inoculated 24 hours before application of chemical.
[5]Not tested.
Note:
Curzate ® is the registered trademark of E.I. du Pont de Nemours & Co. for formulation of 2-Cyano-N-(ethyl-amino) carbonyl)-2-(methoxyimino) acetamide
Manzate ® is the registered trademark of E.I. du Pont de Nemours & Co. for formulations of Magnanese ethylenebisdithio carbamate

TABLE 4

Evaluation of silver diphenyl hydontain for the control of tomato late blight (*Phytophthora infestans*)[1]

| Compound | Concentration[2] | Percent Disease Control |
|---|---|---|
| Silver diphenyl hydantoin | 100 | 98 |
| | 20 | 95 |
| | 5 | 17 |
| Curzate ® | 100 | 100 |
| | 20 | 90 |
| | 5 | 40 |

TABLE 4-continued

Evaluation of silver diphenyl hydontain
for the control of tomato late blight
(*Phytophthora infestans*)[1]

| Compound | Concentration[2] | Percent Disease Control |
|---|---|---|
| Manzate ® | 100 | 100 |
|  | 20 | 90 |
|  | 5 | 0 |

[1]Test plants inoculated with aqueous sporangial suspension (2.0 × 10$^4$ sporangia/ml).
[2]ppm.

TABLE 5

Evaluation of silver diphenyl hydantoin
for the control of apple scab (*Venturia inaequalis*)[1]

| Compound | Concentration[2] | Percent Disease Control Preventive[3] | Curative[4] |
|---|---|---|---|
| Silver | 100 | 100 | 0 |
| diphenyl | 20 | 100 | 0 |
| hydantoin | 5 | 60 | 0 |
| Manzate ® | 100 | 100 | 0 |
|  | 20 | 55 | 0 |
|  | 5 | 12 | 0 |
| Baycor ® | 20 | 100 | 100 |
|  | 5 | 85 | 65 |
|  | 1 | 15 | 40 |

[1]Test plants inoculated with an aqueous conidial suspension (1.5 × 10$^5$ conidia/ml).
[2]ppm.
[3]Test plants inoculated 24 hours after application of chemical.
[4]Test plants inoculated 24 hours before application of chemical.
[5]BAYCOR ® is the registered trademark of Bayer AG (Federal Republic of Germany) and Mobay Chemical Corp., Agricultural Chemicals Division, for formulations of B (1, 1-Biphenyl)-4-yloxy)a (1, 1 dimethylethyl)-1H-1, 2, 4 triazole-ethanol.

TABLE 6

Evaluation of silver diphenyl hydantoin
for the control of peanut leafspot
(*Cercospora arachidicola*)[1]

| Compound | Concentration[2] | Percent Disease Control Preventive[3] | Curative[4] |
|---|---|---|---|
| Silver | 100 | 78 | 60 |
| diphenytoin | 20 | — | 0 |
| hydantoin | 5 | 16 | 0 |
| Manzate ® | 100 | 85 | 0 |
|  | 20 | 30 | 0 |
|  | 5 | 0 | 0 |
| Baycor ® | 20 | 100 | 100 |
|  | 5 | 98 | 100 |
|  | 1 | 77 | 92 |

[1]Test plants inoculated with an aqueous conidial suspension (6.0 × 10$^4$ conidia/ml).
[2]ppm.
[3]Test plants inoculated 24 hours after application of chemical.
[4]Test plants inoculated 24 hours before application of chemical.

Organometallic complexes of diphenyl hydantoin, particularly silver diphenyl hydantoin, are effective against various infectious agents, including bacteria, viruses, fungi, parasites, and insects. It has been found, in particular, that silver diphenyl hydantoin is useful against silver sensitive parasitic infections, including, but not limited to, all species of malaria-carrying plasmodia sporoza. Thus, silver diphenyl hydantoin may be applied in treatement of infections of the blood caused by, e.g., parasites.

Additionally, it is found that diphenyl hydantoin compounds accumulate in tumor cells. Hence, the compound of the invention may be used as well in the delivery of, e.g., Ag, to tumor cells. The accumulated organometallic diphenyl hydantoin complex allows diffusion of the metal ion to the tumor cells, resulting in a gradual release of the material.

The method of delivery of the organometallic complex will vary depending upon the type and extent of the infection being treated or prevented. Topical application may be desirable when the tissue infected exhibits a surface infection such as, e.g., a surface wound or lesion which has been infected. This topical method of application is particularly appropriate in treating plant tissue infections. Application may be accomplished parenterally as well, taking the form, e.g., of subcutaneous injection, intravenous application, intramuscular injection and the like. Parenteral application is particularly well suited for treating animal tissue infections, such as blood or muscle tissue infections. It is also the preferred method of application when gradual release of the organometallic complex is desired, such as in the treatment of tumor cells.

Some embodiments of the organometallic diphenyl hydantoin complex which are suited for topical or parenteral application include, e.g., creams or ointments, wherein one or more inert ingredients are combined with the complex to aid in its delivery to plant and animal tissue. Liquid carriers may be used, such as in water dispersions, intravenous fluids, aerosols and sprays. Additional materials which may be used as sources for the organometallic complexes include dusts, dusting powders, and tinctures of the compounds or compositions containing the compounds.

More extensive media may be used as well, for larger scale protection from infection or infestation. While suspensions of organometallic complexes may be used to spray plants, e.g., when run-off is not an issue, other media, such as plant stakes treated with the compound, or protective covers, and the like may be issued. Similarly, the compounds may be incorporated with or impregnate dressings such as bandages, mosquito or other protective nets. Mortars, and other building materials may also have incorporated or impregnated therein the organometallic complexes. These paints, e.g., will then act to render dwellings, shelters, etc. , more infection proof than previously possible.

As will be apparent to those skilled in the art, many modifications, alterations, and substitutions are possible, in light of the foregoing disclosures, without departing from the spirit of the invention contained herein.

What is claimed is:

1. Silver diphenyl hydantoin ammonium complex.

2. A method of treating a wound or tissue for the prevention or treatment of an infection and to promote healing which comprises administering silver diphenyl hydantoin ammonium complex to said wound or tissue.

3. A method in accordance with claim 2 wherein said silver diphenyl hydantoin ammonium complex is administered topically.

4. A method in accordance with claim 2 wherein said infection is a microbial infection.

* * * * *